United States Patent [19]

D'Angelo et al.

[11] Patent Number: 5,521,882
[45] Date of Patent: May 28, 1996

[54] MEASUREMENT OF FORMATION CHARACTERISTICS USING ACOUSTIC BOREHOLE TOOL HAVING SOURCES OF DIFFERENT FREQUENCIES

[75] Inventors: Ralph D'Angelo, New Fairfield; Christopher V. Kimball, West Redding; Sergio Kostek, Ridgefield; Thomas J. Plona, New Milford; Kenneth W. Winkler, Ridgefield, all of Conn.

[73] Assignee: Schlumberger Technology Corporation, New York, N.Y.

[21] Appl. No.: 298,919

[22] Filed: Aug. 31, 1994

Related U.S. Application Data

[63] Continuation-in-part of Ser. No. 154,645, Nov. 19, 1993, Pat. No. 5,485,431, Ser. No. 220,717, Mar. 30, 1994, and Ser. No. 225,016, Apr. 8, 1994, Pat. No. 5,398,215.

[51] Int. Cl.[6] .................................................. G01V 1/40
[52] U.S. Cl. .............................. 367/32; 367/49; 364/422; 324/335
[58] Field of Search ..................... 367/30–32, 49; 181/105, 111; 364/422, 806; 324/328, 335

[56] References Cited

U.S. PATENT DOCUMENTS

| | | | |
|---|---|---|---|
| 4,012,950 | 3/1977 | Kompfner et al. | 73/646 |
| 4,819,214 | 4/1989 | Gutowski et al. | 367/46 |
| 5,081,611 | 1/1992 | Hornby | 367/27 |

OTHER PUBLICATIONS

Johnson et al., Jour. of Geophys. Research, vol. 92, No. B5, pp. 3597–3602, Apr. 10, 1987.
Johnson et al. J. Geophys. Res, B., vol. 94, pp. 17–729/17–733.
Johnson et al, J. Acoust. Soc. America, vol. 89, #2, Feb. 1991, pp. 598–603.

*Primary Examiner*—Nelson Moskowitz
*Attorney, Agent, or Firm*—David P. Gordon; Martin D. Hyden; Leonard W. Pojunas

[57] ABSTRACT

Apparatus and methods for determining an indication of a nonlinear property of a formation traversed by a borehole are provided. An acoustic tool is used in a borehole to generate first and second signals of different frequencies. As a result of nonlinearities in the formation, the mixing of the first and second signals results in a third signal having a frequency equal to the difference of the frequencies of the first and second signals. The amplitude of the third signal is measured by a detector, and the indication of nonlinearity of the formation is determined according to a relationship which relates the measured amplitude at the measured frequency to the amplitudes of the first and second signals, the frequency of measurement, the velocity of the measured wave, the distance of the receiver from the source, and a function of the nonlinear and linear parameters of the formation. The indication of nonlinearity may then be utilized to give an indication of the relative consolidation of the formation surrounding the borehole.

20 Claims, 2 Drawing Sheets

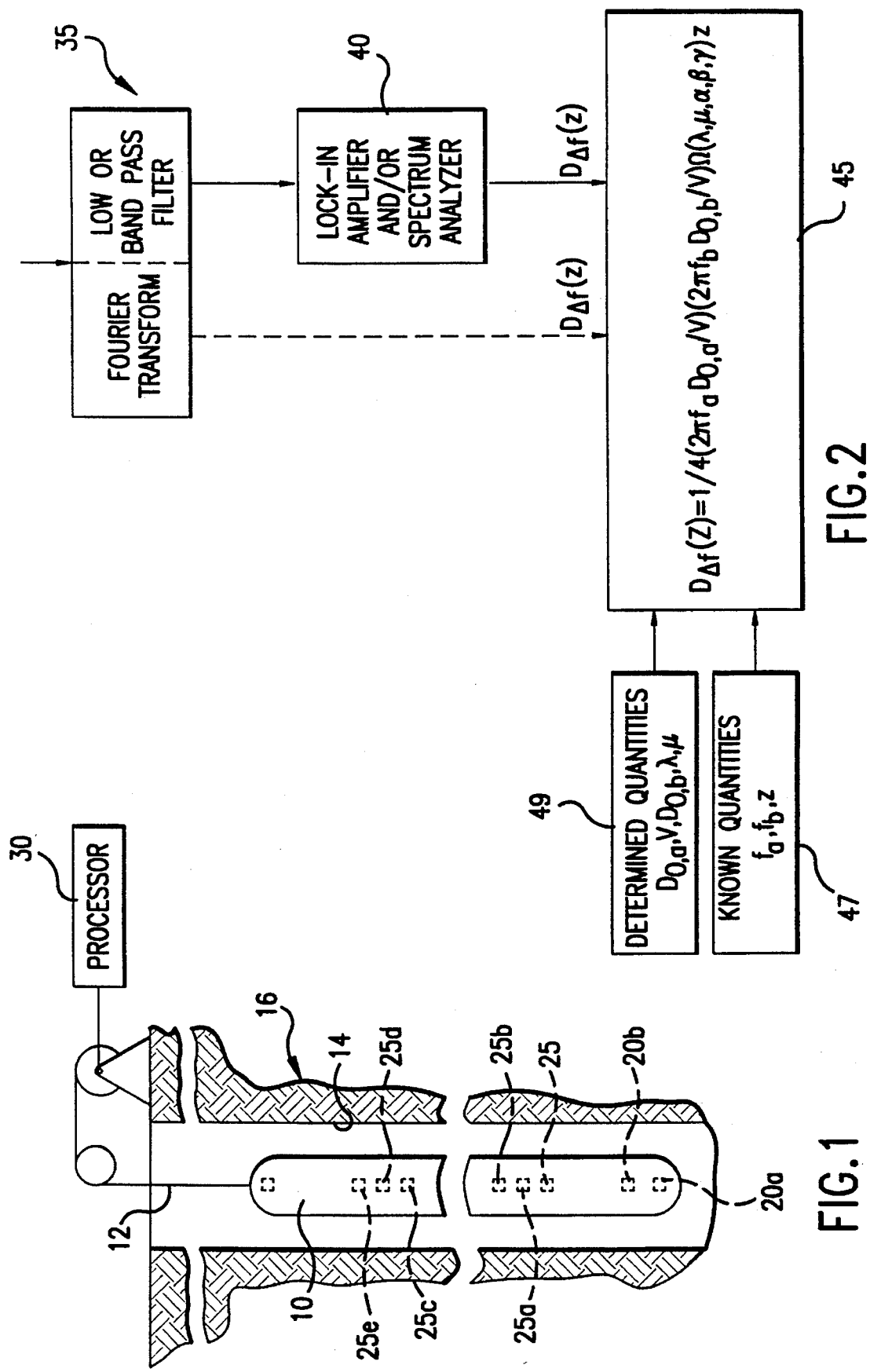

MEASUREMENT OF FORMATION CHARACTERISTICS USING ACOUSTIC BOREHOLE TOOL HAVING SOURCES OF DIFFERENT FREQUENCIES

This is a continuation-in-part of U.S. Ser. No. 08/154,645 now issued as U.S. Pat. No. 5,485,432, U.S. Ser. No. 08/220,717, and 08/225,016 filed respectively on Nov. 19, 1993, Mar. 30, 1994, and Apr. 8, 1994 which are hereby incorporated by reference herein in their entireties.

BACKGROUND OF THE INVENTION

1. Field of the Invention

This invention relates broadly to methods and apparatus for investigating subsurface earth formations. More particularly, this invention relates to acoustic borehole tools and methods for measuring a characteristic of an earth formation. The invention has particular application to the measurement of formation nonlinearity.

2. State of the Art

The art of acoustic well logging for use in determining formation parameters is a well established art. Acoustic well logging generally encompasses both sonic and ultrasonic well logging. Sonic well logs are typically derived from sonic tools suspended in a mud-filled borehole by a cable. The tools typically include a sonic source (transmitter) and a plurality of receivers which are spaced apart by several inches or feet. Typically, a sonic signal is transmitted from the transmitter at one longitudinal end of the tool and received by the receivers at the other, and measurements are made every few inches as the tool is drawn up the borehole. The sonic signal from the transmitter or source enters the formation adjacent the borehole, and the arrival times of the compressional (P-wave), shear (S-wave) and Stoneley (tube) waves are detected by the receivers. The receiver responses are typically processed in order to provide a time to depth conversion capability for seismic studies as well as for providing the determinations of formations parameters such as porosity.

While measurements of the compressional, shear, and tube waves are useful in quantifying various parameters of the formation, it will be appreciated that to date, there has been no successful mechanism for making in situ determinations of nonlinear aspects of the formation. For purposes of this invention, it should be understood that the term "nonlinear" when used to describe a material relates to the fact that a plot of stress versus strain in a material will exhibit some nonlinear behavior. The more nonlinear the stress versus strain plot is, the more nonlinear the material is said to be. Various manifestations of nonlinearity include: the varying of the acoustic velocity in the material when the confining pressure changes; the varying of the acoustic velocity in the material when the amplitude of the acoustic wave changes; the interaction of two monochromatic acoustic beams having different frequencies to create third and fourth acoustic beams having the difference frequency and the additive frequency of the two incident beams; and evidence of frequencies being generated within the material which were not part of any input signal.

In the oil production industry, rock phenomena such as sanding, fracturing and borehole collapse can be considered to relate to the nonlinear properties of the formation. In each case, the strain in the rock catastrophically exceeds that which would be expected from a linear stress-strain relationship. As suggested in one of the parent applications hereto, since the less consolidated a formation is, the more nonlinear it is, a measurement of the nonlinearity of the formation can provide a measurement of the relative state of the consolidation of the formation. As suggested above, whether a layer of a formation is well or poorly consolidated, can broadly affect the producibility of the layer and formation, as well as the manner in Which production is to be carried out.

SUMMARY OF THE INVENTION

It is therefore an object of the invention to provide a measurement of the nonlinearity of a formation traversed by a borehole.

It is a further object of the invention to utilize measurements of acoustic signals having a frequency which is either the difference or sum of two acoustic waves of different frequencies in order to determine an indication of the nonlinearity of the formation.

It is another object of the invention to provide borehole tools having a source or sources of different frequencies and at least one receiver, where the detector detects the amplitude of the difference or sum of the frequencies of the source(s) in order to provide an indication of the nonlinearity of the formation.

It is an additional object of the invention to utilize measurements of acoustic signals in a frequency band which is defined by the sum or difference of two signals occupying disjoint frequency bands in order to determine properties of a formation.

A further object of the invention is to provide an acoustic borehole tool having a source or sources operating in different frequency bands and a receiver which detects the amplitude or phase of the signal in a band centered on either the sum or difference of the source frequencies, where the measured amplitude or phase is taken as an indication of a property of the formation.

Another object of the invention is to compare measured magnitude or phases of sum or difference frequency bands as amplitudes of sources are varied in order to provide indications of formation properties.

In accord with the objects of the invention, an apparatus and a method for determining an indication of a nonlinear property of the formation is provided. The method broadly comprises using an acoustic tool in a borehole to substantially simultaneously generate first and second signals of different frequencies, to measure the amplitude of a signal at a frequency which is either the difference or the sum of the frequencies of the first and second signals, and utilizing the measured amplitude to determine an indication of the nonlinearity of the formation. The indication of nonlinearity of the formation is determined according to a relationship which relates the measured amplitude at the measured frequency to the amplitude(s) of the source(s) of the first and second signals, the frequency of measurement, the velocity of the measured wave, the distance of the receiver from the source(s), and a function of the nonlinear and linear parameters of the formation. The indication of nonlinearity may then be utilized to give an indication of the relative consolidation of the formation surrounding the borehole.

The indication of the nonlinearity of the formation is preferably substantially determined according to a perturbation-derived relationship:

$$D_\Delta(z) = \tfrac{1}{4}(2\pi f_a D_{0,a}/V)(2\pi f_b D_{0,b}/V)\, \Omega(\lambda,\mu,\alpha,\beta,\gamma)z \qquad (1)$$

where $D_{\Delta f}$ is the amplitude of the difference frequency wave measured at the receiver, $f_a$ and $f_b$ are the frequencies of the sources, $D_{0,a}$ and $D_{0,b}$ are the amplitudes of the source(s) at the respective frequencies, V is the velocity of the measured wave in the formation, z is the distance between the source(s) and the receiver, $\Omega$ is a function indicator, $\lambda$ and $\mu$ are the Lamé constants (i.e., linear parameters of the formation), and $\alpha$, $\beta$, and $\lambda$ are nonlinear parameters of the formation which vary as a function of formation stress.

In accord with preferred aspects of the invention, the linear parameters of the formation are measured using conventional techniques, and the amplitudes of the source(s) are calibrated. The transmitters or sources of different frequencies (typically in the 0.1–2000 KHz range) are then excited at a preferably large, calibrated input amplitude, and at the receiver, a measurement is made of the amplitude of the wave received at the difference frequency of the different transmitted sourcing frequencies.. Using an equation such as equation (1) above, an indication of the nonlinearity of the formation can be obtained. If desired, in order to increase the data set, the excitation of the transmitter(s) (and measurements at the receiver) may be repeated while changing the source signal amplitudes. Similarly, a plurality of spaced receivers (i.e., at different distance z) can be utilized to increase the data set. Further, the source(s) can generate p-waves, s-waves, Stoneley waves etc., and measurements of each different type of wave will provide additional unique data indicative of formation nonlinearity. Also, directed ultrasonic sources can be used to excite different modes (e.g., shear and compressional), and detection of difference or sum frequencies can provide yet additional information, including information which provides azimuthal and vertical resolution.

According to other preferred aspects of the invention, in one embodiment of the invention the difference frequency of two source tones (i.e., single frequencies) is utilized in measurement, and the sourcing frequencies of the transmitters are chosen to be similar such that the difference frequency is a low frequency. In this manner, attenuation is limited. In another embodiment of the invention, two preferably non-overlapping frequency spectra are utilized as the sourcing frequencies, and the amplitude or phase of the signal in a band centered on either the sum or difference of the centers of the source frequency spectra is measured, where the measured amplitude or phase is taken as an indication of a property of the formation.

It will be appreciated that the apparatus of the invention relates closely to the method, such that a borehole tool is provided with means for providing acoustic waves of two different sourcing frequencies, means for detecting resulting waves of a difference or sum frequency of the two different sourcing frequencies, and means for processing the detected waves to provide an indication of formation nonlinearity. The acoustic wave apparatus can be incorporated in otherwise conventional borehole logging tools, or in conventional MWD/LWD (measurement/logging while drilling) tools.

Additional objects and advantages of the invention will become apparent to those skilled in the art upon reference to the detailed description taken in conjunction with the provided figures.

BRIEF DESCRIPTION OF THE FIGURES

FIG. 1 is a schematic diagram of the acoustic logging tool of the invention located in a borehole of a formation.

FIG. 2 is a block diagram of the processing utilized to obtain an indication of a nonlinear parameter of the formation according to the invention.

DETAILED DESCRIPTION OF THE PREFERRED EMBODIMENT

Figure 3:
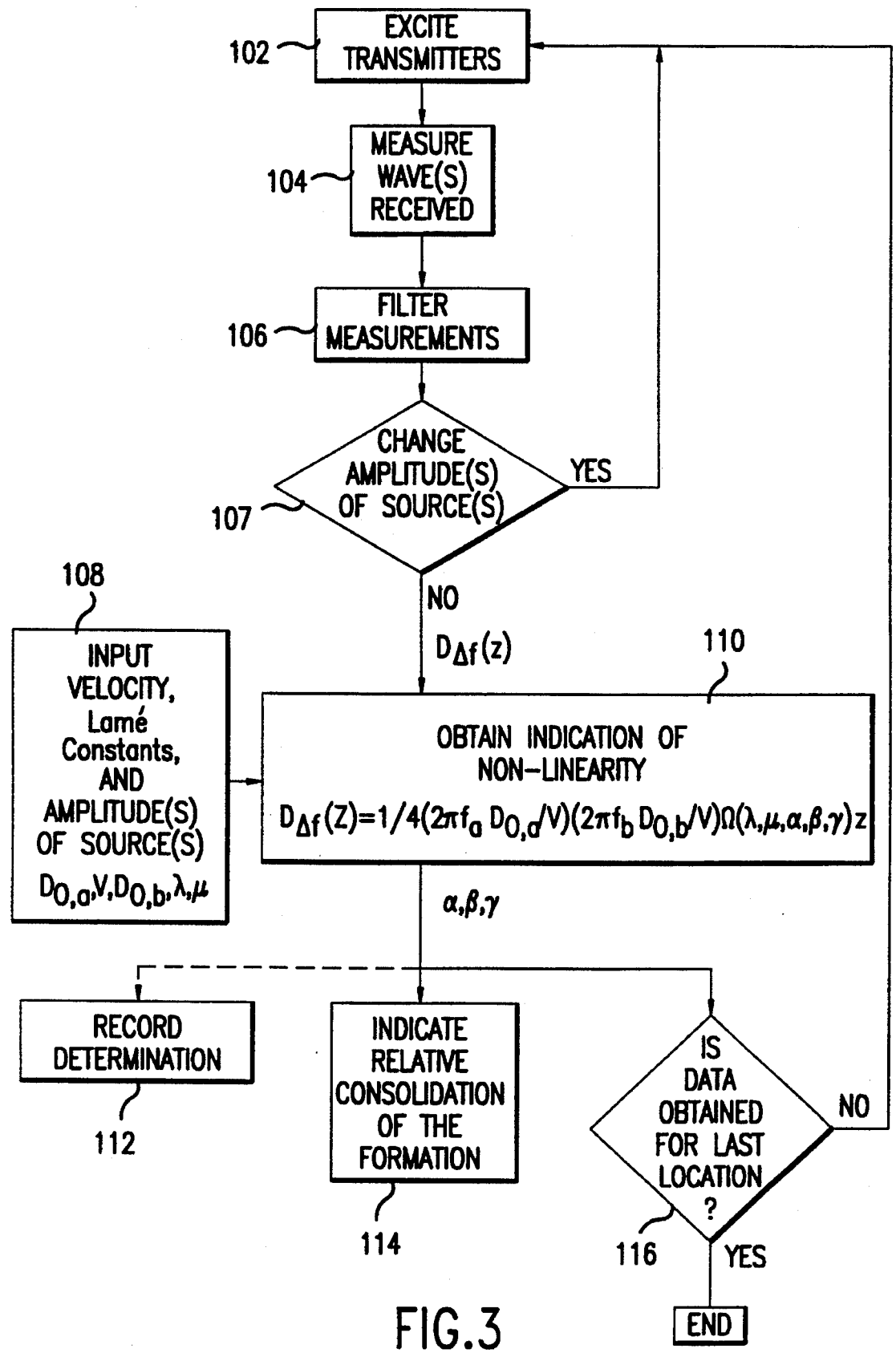
FIG. 3 is a block diagram of the method of the invention for determining an indication of a nonlinear parameter of the formation.

An acoustic logging tool 10 which is suspended from a conventional wireline cable 12 is seen in FIG. 1. The acoustic logging tool 10 is located in a borehole 14 which traverses a formation 16. The acoustic logging tool includes means for producing signals of at least two different acoustic frequencies, which means can take the form of two or more acoustic transmitters (transmitting or sourcing transducers) 20a, 20b, or a single sourcing transducer which can generate at least two distinct frequencies or two bands of frequencies. The acoustic logging tool also includes at least one receiver (detecting pressure transducer) 25. In accord with the invention, the transmitter(s) 20a, 20b are capable of a generating either a pulse, a burst signal (e.g., multiple cycles of a wave), or a continuous wave at one or more different desired sourcing frequencies. The amplitude of the signals produced by the one or more transmitters should be large enough so that a signal at the difference frequency of the source frequencies is detectable in a nonlinear formation by a receiver of the acoustic logging tool as discussed in more detail below. Where two or more transmitters are utilized to generate the two different sourcing frequency signals, the transmitters are typically located substantially adjacent each other. In such a case, it should be appreciated that in order for the raypaths of the transmitters to overlap, either the transmitter 20a must be fired before transmitter 20b (by a time equal to $\Delta X/V$, where $\Delta X$ is the distance between the transmitters, and V is the velocity of the acoustic wave in the formation at the frequencies of interest), or the bursts must be long enough to ensure significant overlap and adequate mixing of the signals in the rock. Regardless, the transmitter(s) are typically located downhole from the receiver(s), and where more than one receiver is provided, the receivers (e.g., 25a, 25b, 25c . . . ) are generally arranged in a longitudinal array. As is well known in the art, each receiver is a pressure transducer which provides as an output an indication of the pressure seen by the transducer as a function of time. Typically, in the acoustic arts, and in accord with the present invention, signals are generated by the transmitters, and the resulting pressure signal detected by the receiver is recorded and processed. The processing may occur downhole by use of a processor (not shown) and/or uphole in processing equipment 30. In a wireline tool, the information is transmitted uphole via the wireline cable 12. In MWD tools, mud pulse telemetry is typically utilized to transmit information uphole. Where information is processed downhole, a microprocessor is typically used. When information is processing uphole, a higher powered processor such as a VAX produced by Digital Equipment Corporation of Brainard, Mass. is often used.

According to the preferred embodiment of the invention, the pressure measured by the receiving transducer is analyzed for its amplitude (and/or phase) at a frequency which is the difference of the sourcing frequencies of the transmitters. While the amplitude of the received signal at the sum of the sourcing frequencies could be utilized, lower frequency signals have less attenuation. Thus, it is expected that the difference frequency will be more easily measurable. It will also be appreciated that harmonics of the difference or sum frequencies could be measured. Again, however, the amplitude of the received signal at these frequencies is expected to be extremely small and hard to measure.

In order to analyze the received signal at the frequency difference, as seen in FIG. 2, the signal obtained by the receiver may either be low- or band-pass filtered or Fourier transformed at 35 to yield the amplitude of the received signal at the desired frequency. While a Fourier transform will provide a direct indication of amplitude at the frequency of interest, it is more computationally intensive. While this is not a problem uphole, in the borehole, and especially in MWD type tools, it is preferred that data processing be kept to a minimum. Thus, where processing is done downhole, it is preferred that the received signal be bandpass filtered, and then provided to a lock-in amplifier and/or analyzed by a spectrum analyzer at 40. Alternatively, as discussed below with respect to pulse signals and broadband processing, the amplitude of the received signal may be integrated over a band of interest to provide an amplitude.

Using the amplitude of the received signal at the difference frequency, an indication of the nonlinearity of the formation can be determined at 45 according to a desired equation. According to the preferred embodiment, the nonlinearity of the formation is determined substantially according to a perturbation-derived relationship for a homogeneous elastic solid as set forth as equation (1) above:

$$D_{\Delta f}(z) = \frac{1}{4}(2\pi f_a D_{0,a}/V)(2\pi f_b D_{0,b}/V)\ \Omega(\lambda,\mu,\alpha,\beta,\gamma)z$$

where $D_{\Delta f}$ is the amplitude of the difference frequency wave measured at the receiver, $f_a$ and $f_b$ are the frequencies of the sources, $D_{0,a}$ and $D_{0,b}$ are the amplitudes of the source(s) at the respective frequencies, v is the velocity of the measured sourcing waves in the formation, z is the distance between the source(s) and the receiver, $\Omega$ is a function indicator, $\lambda$ and $\mu$ are the Lamé constants (i.e., linear parameters of the formation), and $\alpha$, $\beta$, and $\gamma$ are nonlinear parameters of the formation which vary as a function of stress in the formation. It will be appreciated that where the closely spaced sources have the same amplitude, or where a single source having two frequency outputs of the same amplitude is utilized, and the frequencies $f_a$ and $f_b$ are chosen to be close, equation (1) reduces to:

$$D_{\Delta f}(z) = \frac{1}{4}(2\pi f D_0/V)^2\ \Omega(\lambda,\mu,\alpha,\beta,)z \quad (2)$$

While the distance z, and frequencies $f_a$ and $f_b$ are known as indicated at 47, the other elements of equations (1) and (2) must be determined. In particular, as indicated at 49, it is necessary to determine the velocity V, the Lamé constants, and the amplitude(s) $D_0$ of the source(s). The velocity V of the formation may be measured using known borehole tools such as the sonic BHC tool, the LSS tool, the DSI tool, or the SDT tool (BHC, LSS, DSI, and SDT being trademarks of Schlumberger). The Lamé constants $\lambda$ and $\mu$ may be obtained from the determined compressional and shear velocities, as well as a determination of the density ($\rho$) of the formation according to:

$$V_c = \sqrt{(\lambda + 2\mu)/\rho} \quad (3)$$

and $$V_s = \sqrt{\mu/\rho} \quad (4)$$

The density of formation ($\rho$) can be obtained from various known tools of the art, such as the NGT or GST tools (NGT and GST being trademarks of Schlumberger). Finally, it will be appreciated by those skilled in the art, that the amplitude $D_0$ of the source may be obtained via calibration. If a qualitative (relative) determination of nonlinearity is desired, the amplitude $D_0$ does not have to account for attenuation. However, if a quantitative determination of nonlinearity is required, the effective amplitude $D_0$ of the source must be obtained by determining the pressure $P_0$ output by the source (via calibration), and then calculating the appropriate reflection coefficient R. As will be appreciated by those skilled in the art, the reflection coefficient R is a function of the densities of the borehole fluid and formation, and the velocities in the borehole fluid and formation; i.e., $R=((z_2-z_1)/(z_2+z_1))$, where $z_2$ and $z_1$ are respectively the impedances of the formation and the borehole fluid, where the impedance z is equal to $\rho V$. Again, using tools known in the art as well as knowledge of the borehole fluid, each of these variables is either known or may be determined, and $D_0$ may be determined.

Before turning to the method of the invention, it should be appreciated, as mentioned above, that the transmitters of the invention can be pulse sources. Since a single pulse is typically comprised of numerous frequencies, the difference and sum frequencies between two different pulses will generate a higher frequency broadband signal and a lower frequency broadband signal. Preferably, the frequency bands of the source pulses are kept distinct. Regardless, the information is processed preferably by either looking at the amplitude or phase of the signal at the center frequency of the resulting sum or difference broadband signal, or by integrating the energy received over the entire resulting sum or difference broadband signal and utilizing the amplitude of the integration as mentioned above. With respect to the use of phase information, it should be appreciated that the transmitter and receiver circuitry must be synchronized such that any time offset is kept small relative to the period of the received wave. Given the synchronization between the firing of the source and the acquisition of a resulting waveform by the receiver, the phase can be measured in the broad band by examining the phases of the complex spectral values obtained from the Fourier transform (i.e., the phase spectrum) as calculated in the usual manner.

It will also be appreciated that the acoustic transmitters 20a, 20b, . . . can include sonic and/or ultrasonic sources. In the case of sonic sources, the sources are typically omnidirectional (although dipole sources are known), while in the case of ultrasonic sources, the sources are typically directional. It will be appreciated that directional sources can yield azimuthal as well as vertical information.

Turning now to FIG. 3, the method of the invention which is closely tied to the apparatus set forth above is seen. In particular, using a borehole tool such as described above, at 102, one or more transmitters or sources of different frequencies (typically in the 0.1–2000 KHz range) are excited with a pulse, a long tone burst, or a continuous wave, preferably with a large calibrated input amplitude. At 104, measurements are made at the receiver(s) of the amplitude(s) of the wave(s) received. If desired, the receiver(s) can be tuned to look at the difference frequency of the sourcing frequencies, and/or the sum frequency. Otherwise, the measurements of the receiver are filtered at 106 using a Fourier transform, integration, or via bandpass filtering and spectrum analysis to provide an indication of the amplitude of the difference and/or sum frequency. Also, if desired, separate amplitudes for the shear, compressional, and Stoneley waves can be determined at each receiver in a directional or nondirectional manner, with each wave providing unique information regarding formation nonlinearity. If at 107 it is desired to further increase the data set for the borehole depth location (i.e., the distance into the formation), the amplitude of the source or sources may be changed. The method then repeats with steps 102, 104, and 106 as data is gathered and filtered. The cycle may be repeated as many times as desired.

With sufficient difference or sum frequency amplitude data gathered, and with proper inputs 108 such as the formation velocity, the Lamé constants, and the amplitude(s) $D_0$ of the source(s), at 110, an indication of nonlinearity is obtained using an equation such as equation (1) or (2) which relates the amplitude of the sum or difference frequency to the nonlinearity of the formation. If a quantitative determination is desired, the amplitude of the source must not only be calibrated, but the reflection coefficient must be determined as discussed above. Regardless, at 112, either the quantitative or qualitative determination may be recorded. Typically the recordation would take the form of a log of the (relative) amplitude of the nonlinear parameter versus depth in the borehole. At the same time, and based upon the teachings of the parent application hereto, the indication of nonlinearity may be utilized at 114 to give an indication of the relative consolidation of the formation surrounding the borehole. Regardless, at 116, a determination is made whether the data obtained is for a last location in the borehole. If not, the method of the invention returns to step 102, where the entire is procedure is repeated for a new location in the borehole. It will be appreciated that it is possible that the data can be obtained continuously as the borehole tool is dragged up the borehole.

It should be appreciated that the information obtained by the borehole tool of the invention can provide information other than the degree of formation nonlinearity. For example, theoretically, the presence of any signal at either the sum or difference frequency can be taken as a general indication of formation acoustic nonlinearity. The amplitude of the sum or difference frequency band signal for a given source level can then be related to a specific formation property such as the consolidation of the formation, or any other commercially valuable formation characteristic.

There have been illustrated and described herein apparatus and methods for the measurement of nonlinear properties of a formation utilizing an acoustic borehole tool which provides acoustic waves of different frequencies and which measures the amplitude of waves resulting at the difference or sum of the different frequencies. While particular embodiments of the invention have been described, it is not intended that the invention be limited thereto, as it is intended that the invention be as broad in scope as the art will allow and that the specification be read likewise. Thus, while a particular relationship was provided which relates the measured amplitude of the difference or sum frequency with the nonlinearity of the formation, it will be appreciated that the relationship is a relatively crude approximation, as it only directly applies to a homogeneous elastic solid which is subjected to plane waves. Clearly, then, other approximations can be utilized. In fact, with a rigorous analysis of the physics of the borehole and formation, in the vein of that set forth in the parent application hereof, different equations relating the nonlinearity of the formation to the measured difference (or sum) frequency could be utilized. It will be appreciated, however, that any such equation which relates the nonlinearity of the formation to the measured difference or sum frequency will likely include the formation velocity, the Lamé constants, and the amplitude(s) of the source(s). It will therefore be appreciated by those skilled in the art that yet other modifications could be made to the provided invention without deviating from its spirit and scope as so claimed.

We claim:
1. A method for determining via use of a borehole tool an indication of a characteristic of a formation traversed by a borehole, the borehole tool having at least one acoustic source means for transmitting acoustic waves of two different frequencies, at least one acoustic receiver means for measuring the amplitude of a wave at a frequency which is the difference or the sum of the two different frequencies, and processing means, the method comprising:

a) generating with the at least one source means a first acoustic wave at a first frequency and a second acoustic wave at a second frequency different than said first frequency, said first and second acoustic waves mixing in the formation to produce a third acoustic wave having a third frequency equal to at least one of the difference of said first frequency and said second frequency and the sum of said first frequency and said second frequency;

b) detecting with the at least one receiver at least said third acoustic wave at the receiver means;

c) determining with said processing means at least one of an amplitude and a phase of said third acoustic wave having said third frequency; and d) from said at least one of an amplitude and a phase, determining with the processing means an indication of a characteristic of said formation which is a nonlinear property of said formation determined according to the relationship $$D_{\Delta f}(z) = \frac{1}{4}(2\pi f_a D_{0,a}/V)(2\pi f_b D_{0,b}/V)\Omega(\lambda,\mu,\alpha,\beta,\gamma)z$$

where $D_{\Delta f}$ is said amplitude of said third acoustic wave as measured at the receiver, $f_a$ and $f_b$ are said first and second frequencies, $D_{0,a}$ and $D_{0,b}$ are said amplitudes of said first and second acoustic waves, V is said velocity of said third acoustic wave in said formation, z is said distance of the receiver from said at least one source, $\Omega$ is a function indicator, $\lambda$ and $\mu$ are linear formation constants, and $\alpha,\beta$, and $\gamma$ are said nonlinear parameters of the formation.

2. A method according to claim 1, wherein:
said third frequency is equal to the difference of said first frequency and said second frequency, and said first frequency and said second frequency are chosen such that said third frequency is a low frequency such that said third acoustic wave is measurable in the formation.

3. A method according to claim 1, wherein:
said first and second acoustic waves are generated as one of pulses, tone bursts, or continuous waves which mix in said formation.

4. A method according to claim 3, wherein:
said first acoustic wave is generated as a first pulse comprised of a first band of frequencies, and said second acoustic wave is generated as a second pulse comprised of a second band of frequencies.

5. A method according to claim 4, wherein:
said first band of frequencies and said second band of frequencies are substantially non-overlapping.

6. A method according to claim 4, wherein:
said first frequency is taken as a center frequency of said first band of frequencies, and said second frequency is taken as a center frequency of said second band of frequencies.

7. A method according to claim 4, wherein:
said third acoustic wave comprises one of a sum and a difference broadband, and said step of determining includes integrating amplitudes of said third acoustic wave over said broadband.

8. A method according to claim 1, wherein:
said first and second acoustic waves are generated to include at least one of compressional waves, shear waves, and Stoneley waves.

9. A method according to claim 1, wherein:
the at least one receiver comprises a plurality of receivers which are axially spaced from each other, and said step of detecting comprises detecting said third acoustic wave at the plurality of axially spaced receivers.

10. A method according to claim 1, further comprising:
e) repeating steps a) through d) at a plurality of locations in the borehole to provide a plurality of indications of the characteristic of the formation along the length of the formation; and;
f) using said plurality of indications, providing a log of the characteristic.

11. A method according to claim 1, further comprising: calibrating said at least one source.

12. A method according to claim 11, further comprising:
e) repeating steps a) through d) at a plurality of locations in the borehole to provide a plurality of indications of the characteristic of the formation along the length of the formation; and
f) using said plurality of indications, providing a log of the characteristic.

13. A method according to claim 1, further comprising:
at a given depth in the borehole of the formation, changing said amplitude of said first acoustic wave, and said amplitude of said second acoustic wave, and repeating steps a) through d).

14. An apparatus for determining an indication of a characteristic of a formation traversed by a borehole, comprising:
a) source means for generating a first acoustic wave at a first frequency and a second acoustic wave at a second frequency different than said first frequency, said first and second acoustic waves mixing in the formation to produce a third acoustic wave having a third frequency equal to at least one of the difference of said first frequency and said second frequency and the sum of said first frequency and said second frequency;
b) receiver means for detecting said at least said third acoustic wave;
c) processing means coupled to said receiver means for determining at least one of an amplitude and a phase of said third acoustic wave having said third frequency, and for determining from said at least one of an amplitude and a phase, said indication of said characteristic of the formation which is a nonlinear property of said formation which is determined by said processing means according to the relationship $$D_{\Delta f}(z) = \tfrac{1}{4}(2\pi f_a D_{o,a}/V)(2\pi f_b D_{o,b}/V)\Omega(\lambda,\mu,\alpha,\beta,\lambda)z$$

where $D_{\Delta f}$ is said amplitude of said third acoustic wave as measured at the receiver, $f_a$ and $f_b$ are said first and second frequencies, $D_{o,a}$ and $D_{o,b}$ are said amplitudes of said first and second acoustic waves, V is said velocity of said third acoustic wave in said formation, z is said distance of the receiver from said at least one source, $\Omega$ is a function indicator, $\lambda$ and $\mu$ are linear formation constants, and $\alpha,\beta$, and $\gamma$ are said nonlinear parameters of the formation.

15. An apparatus according to claim 14, wherein:
said source means comprises two adjacently located sources, with a first of said two adjacently located sources providing said first acoustic wave, and a second of said two adjacently located sources providing a second acoustic wave.

16. An apparatus according to claim 14, wherein:
said third frequency is equal to the difference of said first frequency and said second frequency, and said first frequency and said second frequency are chosen such that said third frequency is a low frequency such that said third acoustic wave does not substantially attenuate in the formation.

17. An apparatus according to claim 14, wherein:
said source means generates said first and second acoustic waves as one of pulses, tone bursts, or continuous waves which mix in said formation.

18. An apparatus according to claim 14, wherein:
said receiver means comprises a plurality of acoustic detectors which are axially spaced from each other.

19. An apparatus according to claim 14, wherein:
said processing means generates a log of the nonlinear property over depth in said borehole.

20. An apparatus according to claim 14, wherein:
said processing means comprises a filtering means which obtains pressure data from said receiver means, and which filters said pressure data to provides said amplitude at said third frequency of said third acoustic wave.

* * * * *